United States Patent
Lull et al.

(10) Patent No.: US 9,585,820 B2
(45) Date of Patent: *Mar. 7, 2017

(54) LAPONITE CLAY IN COSMETIC AND PERSONAL CARE PRODUCTS

(71) Applicant: Avon Products, Inc., Suffern, NY (US)

(72) Inventors: Michael A. Lull, Pleasantville, NY (US); Ashley L. Howell, Oakland, NJ (US); Candice DeLeo Novack, Monroe, NY (US)

(73) Assignee: Avon Products, Inc., Rye, NY (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/282,392

(22) Filed: May 20, 2014

(65) Prior Publication Data

US 2015/0335544 A1 Nov. 26, 2015

(51) Int. Cl.
*A61K 8/00* (2006.01)
*A61K 8/25* (2006.01)
*A61K 8/73* (2006.01)
*A61Q 17/04* (2006.01)
*A61K 8/02* (2006.01)
*A61K 8/03* (2006.01)

(52) U.S. Cl.
CPC .............. *A61K 8/25* (2013.01); *A61K 8/0229* (2013.01); *A61K 8/03* (2013.01); *A61K 8/731* (2013.01); *A61Q 17/04* (2013.01)

(58) Field of Classification Search
CPC ........ A61K 8/25; A61K 8/731; A61K 8/0229; A61K 8/03; A61Q 17/04
See application file for complete search history.

(56) References Cited

U.S. PATENT DOCUMENTS

| 3,852,076 A | 12/1974 | Grasko |
| 5,470,512 A | 11/1995 | Noji et al. |
| 8,506,953 B2 | 8/2013 | Bottner et al. |
| 8,524,203 B2 | 9/2013 | Polonka |
| 8,586,011 B2 | 11/2013 | Lowndes et al. |
| 8,603,444 B2 | 12/2013 | Bui |
| 2014/0121176 A1* | 5/2014 | Nadau Fourcade ... A61K 8/365 514/33 |

FOREIGN PATENT DOCUMENTS

WO WO 2013048778 A1 * 4/2013 ............. A61K 8/731

* cited by examiner

*Primary Examiner* — Nannette Holloman
(74) *Attorney, Agent, or Firm* — Brian P. McCloskey

(57) ABSTRACT

The invention relates generally to formulations having one or more ingredients segregated from other constituents of the same formulation. The formulations are typically for topical application to an integument.

7 Claims, No Drawings

LAPONITE CLAY IN COSMETIC AND PERSONAL CARE PRODUCTS

FIELD OF INVENTION

The invention relates generally to formulations having one or more ingredients segregated from other constituents of the same formulation. The formulations are typically for topical application to an integument.

BACKGROUND

It has long been considered desirable to provide cosmetics and personal care products that can deliver incompatible ingredients in a single formulation. Generally, the art has utilized systems based on lipids, nanoparticles, microcapsules, and polymeric films to attempt to encapsulate and deliver incompatible actives or other ingredients that are desired to be maintained as separate in a single formulation. Despite prior efforts, there is a continuing need for compositions that are capable of delivering incompatible ingredients.

Laponite clays are synthetic, layered silicates known in the art as additives to cosmetics and personal care products such as foundations, sunscreens, and toothpaste, for their ability to act as thickening agents, gelling agents and fillers (see, e.g., U.S. Pat. Nos. 8,603,444; 8,586,011; 8,524,203; and 8,506,953, the disclosures of which are hereby incorporated by reference). However, heretofore, laponite clays have not been used to segregate discrete ingredients within a single formulation. It is therefore an object of the present invention to provide compositions useful in cosmetics and personal care products that comprise laponite clays and have the ability to deliver two or more ingredients that are incompatible together in a single formulation.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, the present invention provides laponite-clay-containing formulations having one or more ingredients segregated from other constituents of the same formulation, and methods for preparing them. It has surprisingly been found that some ingredients in a cosmetic formulation can be effectively shielded or segregated from other ingredients within the same formulation when such formulations are prepared according to the present invention.

Without wishing to be bound by any particular theory, it is believed that the compositions of the invention have the general form of liquid droplets or globules (e.g., a discontinuous phase) suspended within another liquid (e.g., a continuous phase), wherein discs of laponite clay surround the droplets and are held at the interface between the liquid droplets (e.g., predominantly in edge-to-edge orientation) and the suspending liquid by a thickener (typically polymeric) dissolved in the liquid droplets. This is believed to effectively provide a shell surrounding the liquid droplets which prevents or retards migration of components across the interface. The use of the terms "continuous" and "discontinuous" phases is not to be construed as an emulsion, unless otherwise indicated. The shear (e.g., by rubbing) encountered by the compositions during application is believed to release the contents of the discontinuous phase into the continuous phase. Once released, the contents of the discontinuous phase(s) may blend together with the continuous phase.

Generally, the methods of the invention comprise mixing together (e.g., under low shear or under high shear) a first liquid composition (the continuous phase) comprising water and a laponite clay, and a second liquid composition (the discontinuous phase) comprising water and a polymeric thickener, so that the discontinuous phase forms droplets that are suspended in the continuous phase. The laponite clay (e.g., lithium, magnesium, and sodium silicate; lithium, magnesium, sodium silicate, and tetrasodium pyrophosphate; sodium, magnesium, and fluorosilicate; or sodium, magnesium, fluorosilicate, and tetrasodium pyrophosphate) may comprise between about 0.10% to about 20% (e.g., from about 5% to about 8%) by weight of the total composition. The polymeric thickener (e.g., an acrylate or cellulosic thickener (but not polyethylene glycol) comprises between about 0.10% to about 10% (e.g., from about 0.05% to about 2%) by weight of the total composition). Advantageously, it has been found that components (e.g., those used in cosmetic or personal care formulations, including, for example, water-in-oil or oil-in-water emulsions) can be incorporated into one or both of the phases and are effectively shielded from other components in the same formulation. For example, if a component is added to the second liquid composition (discontinuous phase), the component will remain in the droplets rather than mixing with the first liquid composition (continuous phase). Alternatively, a component incorporated into the first composition (continuous phase), will be shielded and not mix with the components that are in the droplets of the second liquid composition (discontinuous phase). Therefore, it has surprisingly been found that otherwise incompatible components can be delivered in the same formulation (e.g., in the form of a cream, a lotion, or a solid stick) if the components are separated as described (e.g., one component in a droplet of the discontinuous phase and one component in the continuous phase). The interaction between the components in the continuous and discontinuous phase is eliminated, minimized, retarded, etc. In another variant of the invention, the discontinuous phase can be prepared from two or more different liquid compositions, each having different components (e.g., one liquid composition comprising water and a thickener can have a first component, and another liquid composition comprising water and a thickener can have a second component). The components may be incompatible (e.g., titanium dioxide and avobenzone; sodium bicarbonate and an acid) such that together they undergo a chemical or physical interaction. The first and second liquid compositions can be separately added with stirring to the continuous phase to form discrete droplets of the first and second liquid compositions, respectively. In this embodiment too, it has been surprisingly found that interaction between the components is eliminated, minimized, retarded, etc.

In another aspect of the invention, multi-component compositions are provided, comprising a first liquid composition (the continuous phase) that comprises water and a laponite clay, and a second liquid composition (the discontinuous phase) that comprises water and a polymeric thickener, so that the discontinuous phase forms droplets that are suspended in the continuous phase. The laponite clay (e.g., lithium, magnesium, and sodium silicate; lithium, magnesium, sodium silicate, and tetrasodium pyrophosphate; sodium, magnesium, and fluorosilicate; or sodium, magnesium, fluorosilicate, and tetrasodium pyrophosphate) may comprise between about 0.10% to about 20% (e.g., from about 5% to about 8%) by weight of the total composition. The polymeric thickener (e.g., an acrylate or cellulosic thickener (but not polyethylene glycol) that comprises between about 0.10% to about 10% (e.g., from about 0.05% to about 2%) by weight of the total composition). Advantageously, it has been found that components (e.g., those used in cosmetic or personal care formulations, including, for example, water-in-oil or oil-in-water emulsions) can be incorporated into one or both of the phases and are effectively shielded from other components in the same formulation. For example, if a component is added to the second liquid composition (discontinuous phase), the component will remain in the droplets rather than mixing with the first liquid composition (continuous phase). Alternatively, a component incorporated into the first composition (continuous phase), will be shielded and not mix with the components that are in the droplets of the second liquid composition (discontinuous phase). Therefore, it has surprisingly been found that otherwise incompatible components can be delivered in the same formulation (in any kind of cosmetic formulation or personal care product formulation, e.g., in the form of a cream, a lotion, or a solid stick) if the components are separated as described (e.g., one component in a droplet of the discontinuous phase and one component in the continuous phase). The interaction between the components in the continuous and discontinuous phase is eliminated, minimized, retarded, etc. In another variant of the invention, the discontinuous phase can be prepared from two or more different liquid compositions, each having different components (e.g., one liquid composition comprising water and a thickener can have a first component, and another liquid composition comprising water and a thickener can have a second component). The components may be incompatible (e.g., titanium dioxide and avobenzone; sodium bicarbonate and an acid) such that together they undergo a chemical or physical interaction. The first and second liquid compositions can be separately added with stirring to the continuous phase to form discrete droplets of the first and second liquid compositions, respectively. In this embodiment too, it has been surprisingly found that interaction between the components is eliminated, minimized, retarded, etc. Accordingly, another aspect of the invention provides methods for delivering in a single formulation, otherwise incompatible ingredients. The method comprises applying (e.g., by rubbing or blotting, etc.) to a human integument (e.g., skin or hair, such as skin of the face or hands; hair on the head; eyelashes; or eyebrows, etc.) a multi-component composition of the invention.

These and other aspects of the present invention will become apparent to those skilled in the art after a reading of the following detailed description of the invention, including the appended claims.

DETAILED DESCRIPTION

All terms used herein are intended to have their ordinary meaning unless otherwise provided. All ingredient amounts provided herein are by weight percent of the total composition unless otherwise indicated.

By "topically acceptable" is meant that an ingredient is generally regarded as safe and non-toxic for application to a human integument.

It has surprisingly been found that components of a cosmetic or personal care formulation can be effectively shielded or segregated from other components within the same formulation when such formulations are prepared according to the methods of the present invention. As a result, otherwise incompatible constituents can be delivered in the same formulation without spontaneous mixing of the components. The methods generally comprise preparing a multi-component composition by mixing together a first liquid composition, comprising water and a laponite clay (continuous phase), and adding to the first composition, by mixing (or stirring), a second liquid composition, comprising water and a polymeric thickener (discontinuous phase). The discontinuous phase forms droplets that are suspended in the continuous phase. Components such as those used in cosmetics and personal care formulations can be incorporated into the continuous phase, the discontinuous phase, or both phases. When the discontinuous phase is added to the continuous phase, the components in the discontinuous phase remain in the droplets of the discontinuous phase, rather than mixing with the continuous phase.

In the multi-component compositions of the invention, each component in the discontinuous phase is effectively shielded or separated from the continuous phase, so that the interaction between or among them is eliminated, reduced, or retarded compared to an otherwise identical multi-component composition lacking laponite clay. In addition, each component in the discontinuous phase is effectively shielded or separated from every other component in the discontinuous phase, so that the interaction between or among them is eliminated, reduced, or retarded compared to an otherwise identical multi-component composition lacking laponite clay. It is believed that shear (e.g., by rubbing or pressure) that is encountered by the compositions during application, for example, to a human integument, releases the contents of the discontinuous phase into the continuous phase. Once released, the contents of the discontinuous phase may blend together with the continuous phase.

The first liquid composition (continuous phase) in the multi-component compositions of the invention comprises water and at least one laponite clay. Laponite clay refers generally to a synthetic, layered silicate clay that has a layer structure in the form of disc-shaped crystals when dispersed in water. Macromolecules of the laponite clay have a disc-shaped crystal similar to bentonite and hectorite, but are more than one order of magnitude smaller in size. In contrast to clays with a large (e.g., greater than 100) aspect ratio (ratio of length to height) that tend to aggregate in a face-to-face lamellar fashion, laponite clay tends to form partially delaminated disordered aggregates through edge-to-edge interactions. Laponite clay may have, without limitation, an aspect ratio of between about 10 and about 80, or between about 15 and about 50, or between about 20 and about 40, or between about 25 and about 35. In one embodiment, the laponite clay has an aspect ratio of about 30. It will be understood that these aspect ratios represent averages. The surface of the crystal may have a negative charge of about 50-55 mmol·100 $g^{-1}$. The edges of the crystal may have small, localized positive charges that are about 4-5 mmol·100 $g^{-1}$. Laponite clay may have a physical surface area over about 900 $m^2 \cdot g^{-1}$. Laponite clay may comprise about 8% by weight water that may be released from its crystal structure at temperatures above about 150° C. Commonly known laponite clays encompassed by the invention include without limitation those that comprise: lithium, magnesium, and sodium silicate; those that comprise lithium, magnesium, sodium silicate, and tetrasodium pyrophosphate; those that comprise sodium, magnesium, and those that comprise fluorosilicate; and sodium, magnesium, fluorosilicate, and tetrasodium pyrophosphate. Any combination of two or more of these laponite clays may also be used in the multi-component compositions of the invention.

In one embodiment, the diameter of the disc-shaped crystal in the laponite clay may be from about 1 nm to about 300 nm, from about 5 nm to about 150 nm, or from about 10 nm to about 100 nm. In one embodiment, the diameter of the disc-shaped crystal is from about 15 nm to about 50 nm. In another embodiment, the diameter of the disc-shaped crystal is from about 20 nm to about 40 nm, or from about 25 nm to about 35 nm, or about 25 nm, or about 35 nm.

In one embodiment, the thickness of the disc-shaped crystal in the laponite clay may be from about 0.1 nm to about 3 nm, from about 0.5 nm to about 1.5 nm, or from about 0.8 nm to about 1.2 nm. In one embodiment, the thickness of the disc-shaped crystal is from about 0.8 nm to about 1 nm. In another embodiment, the thickness of the disc-shaped crystal is about 0.92 nm. In one embodiment, the density of laponite clay is between about 2.5 and about 2.55 gm/cm$^3$, or about 2.53 gm/cm$^3$.

Non-limiting examples of laponite are disclosed in Herrera et al., J. Mater. Chem., 2005, 863-871; and Cummins, J. Non-Crystalline Solids, 2007, 353, 3891-3905, the disclosures of which are hereby incorporated by reference. Suitable laponites are available from Rockwood Additives as either gel-forming or sol-forming grades. Gels and sols comprising laponites may be thixotropic and/or shear thinning Special mention may be made of the sol forming grade S482.

The amount of laponite clay in the multi-component composition is not particularly limited. For example, the laponite clay may comprise between about 0.01% to about 40% by weight of the total multi-component composition. In other embodiments, the laponite clay comprises between about 0.03% and about 30%, between about 0.05% and about 25%, or between about 0.1% and about 20% by weight of the total multi-component composition. In some preferred embodiments, the laponite clay comprises between about 0.5% and about 10%, between about 1.0% and about 5.5%, or between about 2% and about 4% by weight of the total multi-component composition. In some embodiments, the laponite clay comprises between about 4% and about 10% or between about 5% and about 8% of the total multi-component composition.

The second liquid composition and any additional liquid compositions comprising the discontinuous phase (e.g., third, fourth, fifth liquid compositions, etc.) in the multi-component compositions of the invention may comprise water and at least one polymeric thickener.

The polymeric thickener may be the same or different in each liquid composition of the discontinuous phase, and may comprise, for example, one or more of acrylates copolymers, carboxyvinyl polymers, stearic acid, fatty alcohols, such as cetyl alcohol, stearyl alcohol, carbomers, myristyl stearate, cetyl stearate, magnesium aluminum silicate, polyacrylamide/isoparaffin/laureth-7 (Seppigel), hydroxyethyl cellulose, propylene glycol monostearate, or cellulosic thickeners, including hydroxypropyl cellulose, carboxymethyl cellulose, hydroxyalkyl cellulose, carboxymethylcellulose, and vegetable gums such as xanthan gum and locust bean gum.

Acrylic polymers that may be used as a polymeric thickener include pure acrylic polymers (such as methylmethacrylate and alkyl acrylates, such as butyl acrylate); styrene-acrylic (such as based on styrene and alkyl acrylates, for example, 2-ethylhexyl-acrylate); vinyl acetate copolymers with alkyl acrylate or ethylene or maleates; and styrene-butadiene based polymers, and the like. More particularly, the polymer preferably contains two or more monomers selected from styrene, methylmethacrylate, vinyl acetate, butadiene, n-butyl acrylate, 2-ethylhexyl-acrylate, ethyl-acrylate, methylacrylate, isopropylacrylate, vinyl propionate, dibutyl maleate, ethylene, tert-butyl acrylate, methacrylic acid, acrylic acid, acrylamide, methacrylamide, and hydroxyethyl methacrylate.

In some embodiments, preferred acrylate polymer thickeners comprise high molecular weight acrylate polymers and acrylate copolymers.

In one embodiment, the polymeric thickener comprises hydroxyl ethylcelluose. In another embodiment, the polymeric thickener comprises an acrylate polymer, for example, acrylates/C10-30 alkyl acrylate crosspolymer. In yet another preferred embodiment, the polymeric thickener comprises a carboxyvinyl polymer, for example, Carbopol 940.

In one embodiment, the polymeric thickener does not comprise a polyalkylene oxide such as polyethylene glycol (PEG), or comprises less than about 1% by weight, or less than about 0.5% by weight, or less than about 0.1% by weight of such polyalkylene oxides. In some embodiments, the composition does not comprise a polyalkylene oxide such as PEG, or comprises less than about 1% by weight, or less than about 0.5% by weight, or less than about 0.1% by weight of such polyalkylene oxides.

The amount of the polymeric thickener in the multi-component compositions is not particularly limited, and may comprise, in some embodiments, between about 0.01% and about 25% by weight of the total multi-component composition. In other embodiments, the polymeric thickener may contain between about 0.01% and about 20%, between about 0.5% and about 15%, between about 1% and about 10%, between about 1% and about 8%, between about 1% and about 6%, between about 1% and about 4%, between about 1% and about 2%, or between about 0.5% and about 1% by weight of the total multi-component composition. In some embodiments, the polymeric thickener may contain between about 0.1% and about 2.0%, or between about 0.05% to about 10% by weight of the total multi-component composition.

In preparing the multi-component compositions of the invention, a component may be added to the discontinuous phase, so that it remains in the droplets of the discontinuous phase rather than mixing with the continuous phase. For example, the multi-component composition may comprise a first liquid composition comprising water and a laponite clay, to which is added, with stirring, a second liquid composition comprising water, a polymeric thickener, and a component. The component is shielded from the continuous phase so that that the interaction or mixing of the component and the continuous phase is eliminated, reduced, or retarded compared to an otherwise identical composition lacking the laponite clay.

In another aspect of the invention, a component is added to the continuous phase, and the component does not mix with the components that are in the droplets of the discontinuous phase. For example, the multi-component composition may comprise a first liquid composition comprising water, a laponite clay, and a first component (continuous phase), to which is added, with stirring, a second liquid composition (discontinuous phase) that comprises water, a polymeric thickener, and a second component. The first and second components are shielded from each other such that the interaction between them is eliminated, reduced, or retarded compared to an otherwise identical multi-component composition lacking the laponite clay.

In other embodiments, the discontinuous phase may be prepared from two or more liquid compositions, each liquid composition comprising a different component, and each liquid composition being separately added (with stirring) to the continuous phase. All of the components in the continuous phase (if any) and the discontinuous phase are shielded from one another such that the interaction among them is eliminated, reduced, or retarded compared to an otherwise identical multi-component composition lacking the laponite clay.

The components that are separated or shielded from one another may be chemically incompatible with one another. By chemically incompatible it is meant that together, the components would undergo a chemical or physical reaction or transformation.

In some embodiments, at least some of the components are chemically compatible with one another, and together do not undergo a chemical or physical reaction or transformation.

In some embodiments, the chemically incompatible components comprise an organic sunscreen and an inorganic sunscreen. In one preferred embodiment, the components comprise titanium dioxide and avobenzone.

In another embodiment, the components comprise an acidic and a basic compound that would reach with one another but for the segregation by laponite. For example, the components may comprise sodium bicarbonate and an acid, such as citric acid, glycolic acid, or acetic acid, or the like.

In some embodiments, a first liquid composition may comprise water and a laponite clay (continuous phase), and a second liquid composition (discontinuous phase) may comprise water, a polymeric thickener, and one or more vitamins, such as Vitamin A (Retinol), or Vitamin C. In other embodiments, the second liquid composition may comprise water, a polymeric thickener, and a humectant, such as glycerin. In other embodiments, the second liquid composition may comprise water, a polymeric thickener, and a moisturizer or occlusive, such as polybutene.

The segregation of certain components by the methods of the invention may prevent or diminish or retard the development of discoloration of a formulation. For example, the segregation of Vitamin C from other components in a formulation can prevent a formulation from becoming discolored (e.g., turning yellow).

In some embodiments, the segregation of components by the methods of the invention may help maintain a smooth, or consistent texture in the multi-component composition. For example, the composition may inhibit or prevent flocculation, coagulation, phase separation, syneresis, and the like.

In come embodiments, the components that are shielded or separated from one another are different colored components (e.g., pigments, dyes, lakes, etc.), so that the multi-component composition maintains multiple colors until application to a human integument.

In other embodiments, the components comprise colorants (e.g., pigments, dyes, lakes, etc.), and application (e.g., by rubbing, blotting, or pressing, etc.) of the multi-component composition to a human integument may cause a change in color, a change in hue, a change in shade, or a change in intensity of the color of the multi-component composition. The color change may be affected by a physical blending of colorants, a change in pH, a chemical reaction (e.g., oxidation of a two-part reactive dye), or any other mechanism.

In some embodiments, the methods of the invention provide separation or shielding between or among different kinds of emulsions. For example, the continuous phase liquid composition may comprise water and a laponite clay, and the discontinuous phase comprises two or more liquid compositions, each comprising water, a polymeric thickener, and a different emulsion. In other embodiments, the methods of the invention provide separation or shielding between an emulsion and water. For example, the continuous phase liquid composition may comprise water and a laponite clay, and the discontinuous phases may comprise a polymeric thickener and an emulsion. The components used in the invention may be any kind of emulsion, including, for example, an oil-in-water emulsion, a water-in-oil emulsion, a silicone-in-water emulsion, a water-in-silicone emulsion, etc.

Another aspect of the invention provides multi-component compositions capable of maintaining separation between two or more components. The components in the composition are separated such that the interaction between or among them is reduced, minimized, retarded, etc., compared to an otherwise identical multi-component composition lacking laponite clay. Another aspect of the invention provides multi-component compositions capable of maintaining separation between one or more components in the composition and the continuous phase. The components are separated such that the interaction between or among them is reduced, minimized, retarded, etc., compared to an otherwise identical multi-component composition lacking laponite clay.

The multi-component compositions of the invention may be used in any kind of cosmetic or personal care formulation that can be applied to a human integument. The multi-component composition may be added to any suitable cosmetic formulation or personal care product formulation, whether in the form of a liquid, a cream, a lotion, a solid stick, etc.

For example, the cosmetic composition may be, without limitation, in the form of lipstick, lip color, lip gloss, nail polish, foundation, concealer, blush, eye shadow, eye liner, mascara, bronzer, and the like. The personal care product may be, for example, in the form of day creams or lotions, night creams or lotions, sunscreen lotions, sunscreen creams, sunscreen sprays or oils and other SPF products, moisturizers, salves, ointments, gels, body milks, artificial tanning compositions, shampoos, conditioners, fragrances, and the like.

In one embodiment, the multi-component composition is added to a sunscreen formulation that is in the form of a cream, a spray, or a lotion. In another embodiment, the multi-component composition is added to a solid stick formulation (e.g., a lipstick), which comprises both an inner core and an outer core, the outer core comprising the multi-component composition (in addition to, for example, any suitable waxes described herein) and the inner core comprising, for example, PEG. In yet another embodiment, the multi-component composition is added to a solid stick formulation (e.g., a lipstick), which comprises both an inner core and an outer core, the inner core comprising the multi-component composition (in addition to, for example, any suitable waxes described herein) and the outer core comprising, for example, PEG.

The components shielded in the multi-component compositions of the invention may be any material used in a cosmetic or personal care formulation. The materials described herein can be used as components separated or shielded by the multi-component compositions of the invention, and/or they may be used in a cosmetic formulation or personal care formulation to which the multi-component composition is added.

Sunscreen actives contemplated for use in the compositions of the invention may be organic or inorganic, and/or water-soluble or oil soluble, and include those with UVA and/or UVB absorbance from about 290 to about 400 nanometers solar radiation. Such sunscreen actives include, but are not limited to, one or more of the following: DEA methoxycinnamate, octylmethoxy cinnamate, drometrizole trisiloxane, oxybenzone, octyl methoxycinnamate, octyl salicylate, homomenthyl salicylate, octocrylene, avobenzone, octyl dimethyl PABA, TEA salicylate, 4-methyl benzilidene camphor, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, zinc oxide, titanium dioxide or any derivatives, or any combinations thereof. The sunscreen may be present, for example, from about 1% by weight to about 30% by weight of the total weight of the composition.

In one embodiment, a component shielded or separated by the methods of the invention comprises at least one sunscreen emulsion of which the external phase is aqueous. In another preferred embodiment, at least two sunscreen emulsions are shielded or separated by the methods of the invention, either one or both of which have an external aqueous phase.

Any pigment or combination of pigments may be used in the compositions of the invention. As used herein, the term "pigment" embraces colorants, lakes (FD & C and D & C) and fillers such as talc, calcium carbonate, etc. Exemplary inorganic pigments include, but are not limited to, inorganic oxides (e.g., metal oxides) and hydroxides such as magnesium oxide, magnesium hydroxide, calcium oxide, calcium hydroxides, aluminum oxide, aluminum hydroxide, iron oxides (e.g., $\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxide, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. In one embodiment, the pigments have a particle size from 5 nm to 500 microns, or from 10 nm to 100 microns, or from 100 nm to 30 microns or from about 0.75 to 20 microns. In some embodiments, the particle size (median) will be less than about 10 microns, less than about 5 microns or less than 1 micron.

Other suitable colorants contemplated for use in the invention either as a component to be separated or shielded, or in the final cosmetic or personal care composition, are well known in the art, and are disclosed in the C.T.F.A. Cosmetic Ingredient Handbook, First Edition, 1988, the contents of which are hereby incorporated by reference. Lakes include, for example, FD&C lakes and D&C lakes. Lakes may include those based on barium, strontium, calcium or aluminum. Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI#16035); FD&C Blue #1 (CI#42090); FD&C Yellow #5 (CI#19140); or any combinations thereof.

Additional suitable particulate colorants include carbon black, ultramarine blue, ferric blue, Prussian blue, manganese violet, talc, mica, sericite, calcium carbonate, fumed silica, and the like. Suitable pearling pigments include, without limitation, bismuth oxychloride, guanine, and titanated mica. It may be desirable to employ surface modified pigments to adjust or improve dispersibility, water-resistance, oil-resistance, and the like. For example, pigments may be surface-modified with alkyl silane (e.g., caprylyl silane), Triethoxy Caprylylsilane or Triethoxy Caprylylsilane.

Cosmetic products may include a color component in the form of pigmented solid particles for giving it its characteristic color or "shade," or other solid particles for giving it a desired texture or sheen (e.g., mica, pearlescents, spherical polymers, optical diffusers, waxes, etc.) with the color component being dispersed throughout a suitable base or vehicle. For example, in the case of lipstick the coloring agent or pigmented ingredients may be dispersed in a base comprising a mixture of waxes (typically from 5-20% by weight), emollients, and moisturizers, whereas, in the case of blush, the pigmented solids may be dispersed in a base comprising a mixture of talc, kaolin, and various known binders.

Pearlescents and interference pigments may also be used in the compositions of the invention. Suitable pearling pigments include without limitation, nacre, mica-based pearls, bismuth oxychloride, guanine and titanium composite materials containing, as a titanium component, titanium dioxide, titanium lower oxides or titanium oxynitride. Other suitable pearlescent materials typically are pigments or layers of titanium dioxide on a substrate such as mica, polyethylene terephthalate, bismuth oxychloride, aluminum oxide, calcium borosilicate, synthetic flourophlogopite (synthetic mica), silica, acrylates copolymer, methyl methacrylate, and the like.

The cosmetic compositions and personal care products of the invention may also comprise any conventional components, including fillers and cosmetic powders, film forming polymers, gelling agents, waxes, thickeners, conditioners, actives, solvents, emulsifiers, humectants, emollients, pH adjusters, antioxidants, preservatives, fragrances, and the like. Such components may be present, for example, in an individual or collective amount from about 0.1% to about 30% by weight.

The gelling agent may comprise, for example, one or more of a silicone resin, including Dimethicone/Vinyl Dimethicone crosspolymer, silicone T-resins, ETPEA, polyamides, cellulose ethers (e.g., methyl cellulose or ethyl cellulose) and the like. Thickeners such as acrylates copolymers, hydroxyalkyl cellulose, carboxymethylcellulose, carbomers, and vegetable gums such as xanthan gum may be included.

The compositions may include natural or synthetic film-forming polymers. Suitable polymeric film formers include polyolefins, silicone polymers (e.g., dimethicones, dimethiconols, amodimethicones, silicone resins, etc.), (meth)acrylates, alkyl (meth)acrylates, polyurethanes, fluoropolymers, silicone polyurethanes, and silicone acrylates such as acrylates/dimethicone copolymers. In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. Elastomers formed from ethylene, propylene, butylene, and/or styrene monomers may also be useful. Firm forming polymers may be present from about 0.1% to about 10% by weight of the composition.

Suitable emollients include, without limitation, isopropyl myristate, petrolatum, volatile or non-volatile silicones oils (e.g., methicone, dimethicone), ester oils, mineral oils, hydrocarbon oils, and fatty acid esters. Emollients may comprise from about 0.1% to about 50% by weight of the composition.

Suitable humectants such as polyols (e.g., glycols), including without limitation, glycerin, propylene glycol, ethoxydiglycol, butylene glycol, pentylene glycol, hexylene glycol, caprylyl glycol, and the like. These will typically be added in amount from about 0.001 to about 5% by weight. Humectants, if present, may comprise from about 0.1% to about 50% by weight of the composition.

In another embodiment, the compositions of the invention may also include one or more of the following: a skin penetration enhancer; a skin plumper, such as palmitoyl oligopeptide, collagen, collagen and/or glycosaminoglycan (GAG) enhancing agents; an exfoliating agent; and an antioxidant (e.g., TDPA).

Suitable waxes that may be used alone or in combination include, without limitation, natural waxes, mineral waxes, and synthetic waxes. Natural waxes are those of animal origin, including, without limitation, beeswax, spermaceti, lanolin, and shellac wax, and those of vegetable origin, including, without limitation, carnauba, candelilla, bayberry, and sugarcane wax. Special mention may be made of silicone wax.

Mineral waxes contemplated to be useful include, without limitation, ozokerite, ceresin, montan, paraffin, microcrystalline, petroleum, and petrolatum waxes.

Suitable synthetic waxes which may be used in a final cosmetic product formulation or personal care product formulation (but not for use as a polymeric thickener in the multi-component composition of the invention) include, for example, polyethylene glycols such as PEG-18, PEG-20, PEG-32, PEG-75, PEG-90, PEG-100, and PEG-180 which are sold under the tradename CARBOWAX® (The Dow Chemical Company). Carbowax 1000 has a molecular weight range of 950 to 1,050 and a melting point of about 38° C., Carbowax 1450 has a molecular weight range of about 1,305 to 1,595 and a melting point of about 56° C., Carbowax 3350 has a molecular weight range of 3,015 to 3,685 and a melting point of about 56° C., and Carbowax 8000 has a molecular weight range of 7,000 to 9,000 and a melting point of about 61° C.

Additional suitable synthetic waxes include Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include those sold under the tradename PETROLITE® Copolymers (Baker Hughes Incorporated) with melting points ranging from 95° C. to 115° C.

Waxes may individually or collectively comprise from about 0.1% to about 30% by weight of the composition.

Other suitable materials for use in the invention may include skin benefit agents such as antioxidants (e.g., BHT, ascorbic acid, sodium ascorbate, ascorbyl palmitate, beta-carotene, etc.), vitamins (e.g., tocopherol, tocopheryl acetate, etc.), alpha-hydroxy acids (e.g., glycolic acid), beta-hydroxy acids (e.g., salicylic acid), retinoids (e.g., retinoic acid, all-trans-retinoic acid, retinaldehyde, retinol, and retinol esters such as acetates or palmitates), other anti-aging ingredients (e.g., collagen stimulators, collagenase inhibitors, elastase inhibitors), depigmenting agents (e.g., TDPA, hydroquinone, kojic acid), barrier function enhancing agents (e.g., ceramides, glycerides, cholesterol and its esters, alpha-hydroxy and omega-hydroxy fatty acids and esters thereof, etc.), exfoliating agents, estrogen synthetase stimulating compounds (e.g., caffeine and derivatives), compounds capable of inhibiting 5 alpha-reductase activity (e.g., linolenic acid, linoleic acid, finasteride, and mixtures thereof). These benefit agents will typically be present, if at all, in amounts between about 0.001% and about 10% by weight of the composition.

Additional suitable materials may include botanicals, keratolytic agents, keratinocyte proliferation enhancers, anti-inflammatory agents, steroids, desthiobiotin, piperazine carboxamide, cis-6-nonenol, arginine, glucosamine, algae extract, chlorphenesin, advanced glycation end-product (AGE) inhibitors, and PLOD-2 stimulators (e.g., N-acetyl amino acid amides, such as N-Acetyl Tyrosinamide).

Suitable fillers may include talc, silica, alumina, zinc stearate, mica, kaolin, nylon (in particular orgasol) powder, polyethylene powder, polypropylene powder, acrylates powders, Teflon, starch, boron nitride, copolymer microspheres such as Expancel (Nobel Industrie), Polytrap (Dow Corning), and silicone resin microbeads (Tospearl from Toshiba).

Other suitable fillers include inorganic powders such as chalk, fumed silica, fumed alumina, calcium oxide, calcium carbonate, magnesium oxide, magnesium carbonate, Fuller's earth, attapulgite, bentonite, muscovite, phlogopite, synthetic mica, lepidolite, hectorite, biotite, lithia mica, vermiculite, aluminum silicate, aluminum magnesium silicate, diatomaceous earth, starch, alkyl and/or trialkyl aryl ammonium smectites, chemically modified magnesium aluminum silicate, organically modified montmorillonite clay, hydrated aluminum silicate, hydrated silica, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide; organic powder, cyclodextrin, methyl polymethacrylate powder, copolymer powder of styrene and acrylic acid, benzoguanamine resin powder, and poly(ethylene tetrafluoride) powder. Fillers may comprise from about 0.1% to about 20% by weight of the composition.

The compositions may further include an emulsifier. The amount of emulsifier will typically be from about 0.001 to about 10% by weight, but preferably will range from about 0.01 to about 5% by weight, and most preferably about 0.1 to about 1% by weight, based upon the total weight of the composition. The emulsifier may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few. Additional emulsifiers are provided in the INCI Ingredient Dictionary and Handbook 11th Edition 2006, the disclosure of which is hereby incorporated by reference.

The compositions may comprise a cationic polymer. Cationic polymers include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. When present, the cationic polymer will typically comprise an amount of about 0.1% to about 15% by weight of the composition. In other embodiments the compositions may contain an amount of cationic (quaternium) ingredients that are anhydrous or have very low level of water, e.g., less than 1% by weight. Other suitable quaternium compounds include, without limitation, Polyquaternium-(INCI), Silicone Quaternium-18 (INCI), PEG-2 Dimeadowfoamamidoethylmonium Methosulfate and Hexylene Glycol (INCI), and Cetrimonium Chloride (INCI), to name a few. Such quaternium compounds, if present, will typically comprise from about 0.05% to about 5% by weight of the total composition, and more typically, from about 0.1% to about 1.5% by weight.

The compositions may also comprise monomer quaternary ammonium compounds such as, for example, alkyltrimethylammonium chlorides, dialkylmethyl-ammonium chlorides, alkyldimethylbenzylammonium chlorides, and alkylpyridinium chlorides. In one embodiment, the composition comprises at least one conditioning agent selected from the group consisting of polyquaterniums, cationic polymers, cationic surfactants, non-volatile dimethicone oils, dimethiconols, amodimethicones, ester oils, fatty alcohols, cationic gums and cellulosics, amido amines, cetrimonium chloride, behentrimonium chloride, stearamidopropyl dimethylamine, polyesteramines, and cationically charge-modified polymers derived from guar gum, cellulose, proteins, polypeptides, chitosan, lanolin, starches and amino silicones.

The compositions may include a nonionic surfactant such as Laureth-23, Ceteth-10, Ceteth-20, IsoCeteth-20, Steareth-20, Oleth-10, Oleth-20, or alkyl polyglucose. The nonionic surfactant may be formed from a fatty alcohol, a fatty acid, or a glyceride with a C8 to C24 carbon chain. The compositions of the invention can further comprise proteins, peptides, and amino acids including hydrolyzed soy protein, lauryldimonium hydrolyzed soy protein (cationic Soya protein), wheat amino acids, corn, wheat, milk, or silk proteins, collagens, keratins, taurine and arginine hydrochloride, etc.

The cosmetic compositions of the invention may optionally include one or more agents that provide or enhance shine on a keratin fiber. Shine enhancing agents will typically have a refractive index greater than about 1.4, preferably greater than about 1.5 when measured as a film at 25° C. Suitable shine enhancing agents include without limitation, polyols, fatty esters, silicone phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, based on the total weight of the composition.

The compositions may also comprise a preservative or anti-microbial agent, for example, methylchloroisothiazolinone, methylisothiazolinone, methylparaben, propylparaben, phenoxyethanol, or caprylyl glycol.

The compositions of the invention may include a cosmetically or dermatologically acceptable vehicle that is substantially anhydrous. As used herein, "substantially anhydrous" means comprising less than 5% water. In other embodiments, the vehicle and/or the entire cosmetic or personal care composition comprises less than 4%, less than 3%, less than 2%, less than 1%, less than 0.5%, or less than 0.1% by weight water.

The vehicle may be in the form of, for example, a serum, a cream, a lotion, a gel, or a stick, and may comprise an emulsion (e.g., polyol-in-silicone, silicone-in-polyol emulsion, etc.), or may comprise an ethanolic vehicle, silicone (e.g., cyclomethicone, dimethicone, etc.), hydrocarbon (e.g., petrolatum, isododecane, etc.), ester oil (e.g., isopropyl myristate, myristyl myristate), or the like. The vehicle may further comprise an emulsifier, gelling agent, structuring agent, rheology modifier (e.g., a thickener), film former, or the like. The vehicle may comprise from about 25% to about 99% by weight of the composition.

In another aspect of the invention, methods are provided for delivering one or more components in a single formulation. In some embodiments, methods are provided for delivering in a single formulation, otherwise incompatible ingredients. The method comprises applying to a human integument a multi-component composition of the invention, comprising a first liquid composition (continuous phase) that comprises water and a laponite clay, and a second liquid composition (discontinuous phase) that comprises water and a polymeric thickener. The compositions are applied to a human integument for example, by the application of pressure or shear, such as by rubbing, blotting, or patting, etc. Application of the composition can release the contents of the discontinuous phase into the continuous phase, so that the contents of the discontinuous phase can blend together with the continuous phase. The amount of pressure applied during rubbing and the duration of rubbing needed will vary based on the particular components and, for example, the desired look, shine, color, or texture.

The multi-component compositions of the invention may be applied to the human integumentary system, including, for example, skin, lips, nails, hair, and other keratinous surfaces. As used herein, the term "keratinous surface" refers to keratin-containing portions of the human integumentary system, which includes, but is not limited to, skin, lips, hair (including hair of the scalp, eyelashes, eyebrows, facial hair, and body hair such as hair of the arms, legs, etc.), and nails (toenails, fingernails, cuticles, etc.) of mammalians, preferably humans.

The multi-component compositions of the invention can be applied to any area of the skin, and preferably to the face, the neck, the hands, the feet, or other areas of the body, such as arms, legs, and back.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

Example 1

A multi-component sunscreen product was prepared according to the methods of the invention, comprising two incompatible sunscreen emulsions: an organic sunscreen and a mineral-based sunscreen. Separation of the organic sunscreen and the mineral-based (inorganic) sunscreen was maintained in the final sunscreen product by the methods of the invention described herein. The formulation for the organic sunscreen is shown below in Table 1.

TABLE 1

Organic Sunscreen

| Ingredient | Amount (w/w % in formulation) |
|---|---|
| PART A | |
| DEMINERALIZED WATER | 64.905 |
| ACRYLATES/C10-30 ALKYL ACRYLATE CROSSPOLYMER | 0.200 |
| CARBOPOL 940 | 0.250 |
| HYDROXYETHYL CELLULOSE | 0.250 |
| DISODIUM EDTA | 0.200 |
| BUTYLENE GLYCOL | 1.500 |
| GLYCERIN | 3.000 |
| METHYLPARABEN | 0.400 |
| LECITHIN 65% | 0.300 |
| BENZOPHENONE-3 (OXYBENZONE) | 5.500 |
| PART B | |
| HOMOMENTHYL SALICYLATE | 8.000 |
| BUTYL METHOXYDIBENZOYLMETHANE- 100% | 2.800 |
| OCTOCRYLENE | 2.500 |
| OCTYL SALICYLATE | 4.750 |
| POLYGLYCERYL-3 DIISOSTEARATE- LOW ODOR | 0.200 |
| CETYL ALCOHOL | 0.600 |
| POE (24M) CHOLESTEROL ETHER | 0.125 |
| GLYCERYL STEARATE- 90% MONOESTER | 0.400 |
| OCTYL ISONONANOATE | 1.000 |
| SILICA-FUMED | 0.100 |
| PART C | |
| DIMETHYL/TRIMETHYL POLYSILOXANE | 1.000 |
| ISODODECANE | 1.500 |
| SILICONE RESIN-DIMETHYLMETHYL | 0.120 |
| PART D | |
| TRIETHANOLAMINE 99% | 0.600 |
| PART E | |
| PHENOXYETHANOL | 0.500 |

The organic sunscreen was made by preparing each of Parts A through E, the ingredients of which are shown in Table 1. Part A was prepared by first adding the demineralized water to a main kettle, and then adding the remainder of the Part A ingredients under high sheer mixing until dispersed. Part A was heated to 65° C. with continued mixing. Part B was prepared in a separate vessel, heated to 75° C., and mixed until homogeneous. Part B was then slowly added to Part A (in the main kettle), and mixing was maintained. Part C ingredients were added one at a time to the main kettle and mixed until combined. The main kettle was then cooled to 45° C. Part D ingredients were then added to the main kettle and mixed. The main kettle was then cooled to 35° C. Part E ingredients were then added and mixed until completion.

The formulation for the mineral-based sunscreen is shown below in Table 2.

TABLE 2

Mineral-Based Sunscreen

| Description | Amount (w/w % in formulation) |
|---|---|
| PART A | |
| DEMINERALIZED WATER | 68.480 |
| ACRYLATES/C10-30 ALKYL ACRYLATE CROSSPOLYMER | 0.200 |
| CARBOPOL 940 | 0.250 |
| HYDROXYETHYL CELLULOSE | 0.250 |
| DISODIUM EDTA-TECH.GRADE | 0.200 |
| BUTYLENE GLYCOL | 1.500 |
| GLYCERIN | 3.000 |
| METHYLPARABEN | 0.400 |
| LECITHIN 65% | 0.500 |
| PART B | |
| TITANIUM DIOXIDE/ISODECYL ISONONANOATE/ISOCETYL STEAROYL STEARATE/PHENYL TRIMETHICONE- BLEND | 8.500 |
| ZINC OXIDE/ISODECYL ISONON/ISOCETYL STEAROYL STEAR/PHENYL TRIMETH/TRIETHOXY (2.5%) | 10.250 |
| POLYGLYCERYL-3 DIISOSTEARATE- LOW ODOR | 0.500 |
| CETYL ALCOHOL | 0.600 |
| POE (24M) CHOLESTEROL ETHER | 0.250 |
| GLYCERYL STEARATE- 90% MONOESTER | 1.000 |
| OCTYL ISONONANOATE | 1.000 |
| SILICA-FUMED | 0.100 |
| PART C | |
| DIMETHYL/TRIMETHYL POLYSILOXANE | 1.000 |
| ISODODECANE | 1.500 |
| SILICONE RESIN-DIMETHYLMETHYL | 0.120 |
| PART D | |
| TRIETHANOLAMINE 99% | 0.600 |
| PART E | |
| PHENOXYETHANOL | 0.500 |

The mineral-based sunscreen was made by preparing each of Parts A through E the ingredients of which are shown in Table 2. Part A was prepared by first adding the demineralized water to a main kettle, and then adding the remainder of the Part A components under high sheer mixing until dispersed. Part A was heated to 65° C. with continued mixing. Part B was prepared in a separate vessel, heated to 75° C., and mixed until homogeneous. Part B was then slowly added to Part A (in the main kettle), and mixing was maintained. Part C ingredients were added one at a time to the main kettle and mixed until combined. The main kettle was then cooled to 45° C. Part D ingredients were then added to the main kettle and mixed. The main kettle was then cooled to 35° C. Part E ingredients were then added and mixed until completion.

The final formulation for the multi-component sunscreen product is shown below in Table 3.

TABLE 3

Final Multi-Component Sunscreen Formulation

| Description | Amount (w/w % in formulation) |
|---|---|
| PART A | |
| DEMINERALIZED WATER | 56.700 |
| LAPONITE CLAY (SODIUM MAGNESIUM FLUROSILICATE) | 5.000 |
| PART B | |
| PHENOXYETHANOL-98% MIN (*RI*) | 0.500 |
| PART C | |
| DOMAIN 2-MINERAL SUNSCREEN PHASE | 18.900 |
| PART D | |
| DOMAIN 1-ORGANIC SUNSCREEN PHASE | 18.900 |

Part A was prepared by adding demineralized water to a main beaker and mixing, and then adding in the laponite clay until dispersed in the water. Mixing was continued for 20-30 minutes to allow for delamination of the laponite clay. Part B was then added to Part A and mixed until combined. The Part C ingredients (the mineral-based sunscreen) were slowly added to the main beaker at a controlled pace using a pipette. The Part D ingredients (the organic sunscreen) were then slowly added to the main beaker at a controlled pace using a pipette.

The resulting sunscreen product maintains separation (shielding) between the two chemically incompatible sunscreen emulsions, such that they can be present within the same formulation, and maintain efficacy throughout manufacture, storage, and application to a human integument.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

What is claimed:

1. A method of delivering two or more components to a human integument comprising:
    applying to said human integument a multi-component composition comprising:
    (a) a first liquid composition comprising water, a laponite clay, and a first component;
    (b) a second liquid composition comprising water, a polymeric thickener, and a second component;
    wherein said first and second components are separated such that the interaction between them is reduced compared to an otherwise identical multi-component composition lacking the laponite clay, wherein said first and second components are chemically incompatible.

2. The method of claim 1, further comprising (c) a third liquid composition comprising water, a polymeric thickener, and a second component.

3. The method of claim 1, wherein the laponite clay comprises sodium magnesium fluorosilicate.

4. The method of claim 1, wherein the laponite clay comprises from about 1-30% by weight of the composition.

5. The method of claim 1, wherein the laponite clay comprises from about 2-20% by weight of the composition.

6. The method of claim 1, wherein the laponite clay comprises from about 5-10% by weight of the composition.

7. The method according to claim 1, wherein said chemically incompatible components comprise an organic sunscreen and an inorganic sunscreen.

\* \* \* \* \*